(12) United States Patent
Omari et al.

(10) Patent No.: US 11,037,654 B2
(45) Date of Patent: Jun. 15, 2021

(54) RAPID GENOMIC SEQUENCE CLASSIFICATION USING PROBABILISTIC DATA STRUCTURES

(71) Applicant: NOBLIS, INC., Reston, VA (US)

(72) Inventors: Masooda Omari, Fairfax, VA (US); Tyler W. Barrus, Midlothian, VA (US); Mark Sanders, Ashburn, VA (US); Daniel Negron, Reston, VA (US)

(73) Assignee: NOBLIS, INC., Reston, VA (US)

( * ) Notice: Subject to any disclaimer, the term of this patent is extended or adjusted under 35 U.S.C. 154(b) by 84 days.

(21) Appl. No.: 15/977,667

(22) Filed: May 11, 2018

(65) Prior Publication Data

US 2018/0330054 A1    Nov. 15, 2018

Related U.S. Application Data

(60) Provisional application No. 62/505,436, filed on May 12, 2017.

(51) Int. Cl.
| | |
|---|---|
| G16B 30/10 | (2019.01) |
| G16B 30/00 | (2019.01) |
| G06F 16/9038 | (2019.01) |
| G06F 16/903 | (2019.01) |
| G16B 40/00 | (2019.01) |

(52) U.S. Cl.
CPC ......... *G16B 30/00* (2019.02); *G06F 16/9038* (2019.01); *G06F 16/90344* (2019.01); *G16B 30/10* (2019.02); *G16B 40/00* (2019.02)

(58) Field of Classification Search
None
See application file for complete search history.

(56) References Cited

U.S. PATENT DOCUMENTS 8,290,972 B1   10/2012  Deshmukh et al.
8,898,204 B1   11/2014  Sathe et al.
(Continued)

OTHER PUBLICATIONS

Barrus, U.S. Office Action dated Aug. 24, 2020, directed to U.S. Appl. No. 15/977,646; 29 pages.
(Continued)

*Primary Examiner* — Hau H Hoang
(74) *Attorney, Agent, or Firm* — Morrison & Foerster LLP

(57) ABSTRACT

Techniques for identifying and/or classifying genomic information are provided. In some embodiments, genomic information may be identified by computing systems without access to a database of reference genomic information, instead relying on locally stored probabilistic data structures representing reference genomic information. Query genomic data, such as data taken from a read-set, may be divided into sub-strings, and each of the locally-stored probabilistic data structures may be queried by each of the extracted sub-strings, generating probabilistic outputs indicating either that (a) the sub-string is probably included in the set of data represented by the probabilistic data structure or (b) the sub-string is definitely not included in the set of data. Based on the number and/or proportion of sub-strings from a read-set that are indicated as being likely represented by a probabilistic data structure, a likely identity or classification for the genomic information in the read-set may be determined.

15 Claims, 3 Drawing Sheets

(56) References Cited

U.S. PATENT DOCUMENTS

| | | |
|---|---|---|
| 9,817,944 B2 | 11/2017 | Kural |
| 10,642,994 B1 | 5/2020 | Allen et al. |
| 10,790,984 B1 | 9/2020 | Stiles |
| 2008/0040047 A1 | 2/2008 | Nelson et al. |
| 2008/0306694 A1 | 12/2008 | Izmailov et al. |
| 2008/0313132 A1 | 12/2008 | Hao et al. |
| 2009/0030895 A1 | 1/2009 | Eswaran et al. |
| 2009/0241187 A1 | 9/2009 | Troyansky |
| 2011/0098193 A1 | 4/2011 | Kingsmore et al. |
| 2011/0225191 A1 | 9/2011 | Xie |
| 2013/0244614 A1 | 9/2013 | Santamaria et al. |
| 2014/0238937 A1 | 8/2014 | McGinnis |
| 2014/0274752 A1* | 9/2014 | Blume .................. G16B 35/00 506/8 |
| 2015/0220684 A1* | 8/2015 | Greenfield ............ G16C 99/00 707/722 |
| 2016/0132640 A1* | 5/2016 | Layer .................... G16B 20/00 706/12 |
| 2016/0179893 A1 | 6/2016 | He |
| 2016/0344849 A1 | 11/2016 | Thomas |
| 2017/0068776 A1* | 3/2017 | Godinez-Moreno .... G16B 5/00 |
| 2017/0070492 A1 | 3/2017 | Rubin et al. |
| 2018/0011852 A1 | 1/2018 | Bennett et al. |
| 2018/0089365 A1 | 3/2018 | Beal et al. |
| 2018/0248698 A1 | 8/2018 | Kominar et al. |
| 2018/0330052 A1 | 11/2018 | Barrus |
| 2019/0155835 A1 | 5/2019 | Daugharthy et al. |
| 2019/0236267 A1 | 8/2019 | Sanders et al. |
| 2019/0318807 A1 | 10/2019 | O'Hara et al. |

OTHER PUBLICATIONS

Bloom, B.H. (Jul. 1970). "Space/Time Trade-offs in Hash Coding with Allowable Errors," Communications of the ACM 13(7): 422-426.

Hellman, M.E (Jul. 1980). "A Cryptanalytic Time-Memory Trade-Off," IEEE Transactions on Information Theory 26(4): 401-406.

Barrus, U.S. Office Action dated Dec. 22, 2020, directed to U.S. Appl. No. 15/977,646; 14 pages.

* cited by examiner

200

230 - At a local computing system:

232 - Receive plurality of probabilistic data structures and metadata from remote computing system 234 - Receive query data representing one or more query nucleic acid sequences 236 – For each of the plurality of query nucleic acid sequences, divide query nucleic acid sequence into plurality of query sub-strings 238 - Query sub-strings are of predetermined length $k$, where $k$ is the number of bases in a sub-string 240 - Query nucleic acid sequence is divided into $(L - k + 1)$ sub-strings, where $L$ is the number of bases in the query nucleic acid sequence 242 - For each of the plurality of query nucleic acid sequences, store data representing one or more of the plurality of query sub-strings 244 - Store data representing only unique query sub-strings 246 – Storing data representing one or more of the plurality of query sub-strings comprises generating and storing data corresponding to a reverse compliment of one or more of the query sub-strings 248 - For each of the plurality of probabilistic data structures received:

250 - Query probabilistic data structure by data comparing each of the one or more of the plurality of query sub-strings of the query nucleic acid sequence 252 - Generate and store, in response to the querying by each of the one or more query sub-strings, result data indicating whether the set of reference sub-strings includes data corresponding to each of the respective query sub-strings 254 - Calculate proportion query sub-strings that correspond to one or more reference sub-strings represented by the probabilistic data structure

FIG. 2B

RAPID GENOMIC SEQUENCE CLASSIFICATION USING PROBABILISTIC DATA STRUCTURES

REFERENCE TO RELATED APPLICATIONS

This application claims the benefit of U.S. Provisional Application No. 62/505,436, entitled, "RAPID GENOMIC SEQUENCE CLASSIFICATION USING PROBABILISTIC DATA STRUCTURES," filed May 12, 2017, the entire contents of which are incorporated herein by reference.

FIELD OF THE INVENTION

This relates generally to analyzing genomic information, and more specifically to classifying genomic information using probabilistic data structures.

BACKGROUND OF THE INVENTION

Whole genome sequencing (WGS) has made a significant contribution to microbial identification. This technology has made significant advances in accuracy and reproducibility and has considerably reduced costs of microbial identification. These advances make sequencing the entire genome of a microbe attainable for most research laboratories and some clinical laboratories. Additionally, the physical size of sequencing and the complexity of machines and supporting apparatus have been considerably reduced, making the technology more mobile so that it may be feasible to bring the instrument to the sampling location.

As next-generation sequencing (NGS) technologies have matured into third-generation sequencing, advances include faster run times, longer read lengths, and reduced operating costs. This generation is driven by Ion semiconductor, single-molecule real-time, and nanopore sequencing. These systems have also been successfully used in detecting epigenetic modifications.

Sequencing has thus become a widely accepted method of identifying and characterizing numerous and diverse types of organisms and disorders. As databases fill with the resulting sequencing information, our understanding rapidly expands as to how the properties of an organism are driven by the organism's underlying genome. Enough information has been collected to create specialized databases of genes and sequences correlating with interesting properties, such as antibiotic resistance.

Known solutions for applying the information available in genomic information databases to readsets, test data, and other query data against which the database genomic information may be compared have included using various exact and approximate string matching algorithms that may require large compute resources to perform the organism identification. Known solutions use very large computational resources and/or memory requirements to perform the work. BLAST, for example, performs various string matching and indexing approaches. Because sophisticated and expensive computational resources are required for genomic analysis in many cases, practitioners and researchers without direct access to such resources are required to send their unidentified genomic data to central locations for remote analysis.

SUMMARY OF THE INVENTION

As described above, known solutions for comparing genomic information, particularly for comparing whole genome sequencing data stored in databases to new and/or unknown genomic data samples, are time-consuming and computationally intensive. Challenges exist in the design and implementation of systems, methods, and techniques to take advantage of the voluminous genomic information available due to widespread proliferation of WGS technology. In a clinical or public-health setting, rapid turnaround time in identification and analysis is critical, and increasing speed while maintaining accuracy is essential; reducing the time required for genomic analysis of pathogens may help clinicians determine the correct course of treatment, and appropriate administration of antibiotics helps minimize the threats from diseases, including the growing threat of antibiotic resistance pathogens. Another challenge arises in the storage requirements for this expansive amount of genomic data.

Thus, the ability to perform analysis and identification of unidentified genomic data may be restricted to those who have direct access to sophisticated computational resources, or to those who have access to data communication infrastructure capable of transferring large amounts of data to and from said sophisticated computational resources. Accordingly, the ability to perform analysis and identification of unidentified genomic data may be expensive for many and may be completely inaccessible to some (e.g., those in remote areas with poor telecommunications infrastructure).

Thus, there is a need for systems, methods, and techniques that allow for genomic data representing unidentified genomic material to be compared to reference genomic data that is identified with known genomic material, in order to rapidly identify the unknown genomic material. There is a need for systems, methods, and techniques that achieve this aim in a faster, more inexpensive, and more computationally efficient manner. There is a need for systems, methods, and techniques that enable rapid (e.g., within a clinically effective timeframe, such as hours rather than days) and accurate identification of unidentified genomic data with consumer-grade computing resources and without the need for access to supercomputing resources and/or high-speed data uplinks, which may enable deployment of genome identification systems in a variety of scenarios such as emergency outbreak responses, doctor's offices, remote clinics, food safety applications, and other scenarios without access to high-performance computing resources. The systems, methods, and techniques disclosed herein, which include innovated approaches for identifying pathogens and ABR variants using probabilistic data structures and high-speed read-mapping, may address these needs.

In some embodiments, genomic reference data may be encoded and compressed through the use of probabilistic data structures, where each one of a library of reference nucleic acid sequences (e.g., WGS data) may be transformed into a respective probabilistic data structure, which may occupy substantially less space when saved on disk than the original reference nucleic acid sequence data. While the full library of reference nucleic acid sequence data may be accessible only at a high-performance computing system or at a computing system with access to high-speed network connections, and while the encoding and compression may be carried out at that system, the plurality of probabilistic data structures representing encoded and compressed reference nucleic acid sequence data may then be transmitted to and/or stored on a computer storage of a consumer-grade and/or non-network accessible computer system. Without the need for further communication with or reliance on network connections and/or high-performance processing capabilities of remote computing systems, the consumer-grade and/or non-network accessible computer system may then access the plurality of probabilistic data structures in local storage and perform computation and comparisons with query genomic data based on the probabilistic data structures.

As explained herein, unidentified genomic data (e.g., query genomic data) may be compared to each one of the plurality of probabilistic data structures to generate output indicating a level of similarity between the query data and the reference nucleic acid sequence data represented by the respective probabilistic data structure. After comparing the query data to all of the probabilistic data structures, the system may determine that the probabilistic data structure to which the query genomic data is the most similar represents a likely identity of the organism represented by the query genomic data. That is, the system may identify the unknown genomic data as the organism corresponding to the reference genome to which it most closely corresponds.

As explained herein, probabilistic data structures may be used to enable such comparisons and processing without the requirement of long processing times, high-performance supercomputers, and/or high-speed data access.

In some embodiments, a system for identifying genomic information in a computing environment remote from a database of genomic reference data is provided, the system comprising: one or more processors; a memory storing one or more programs, the one or more programs configured to be executed by the one or more processors and including instructions to: receive encoded data representing genomic reference data of a plurality of organisms, wherein the encoded data comprises: a plurality of probabilistic data structures each corresponding respectively to an organism of the plurality of organisms, wherein each of the plurality of probabilistic data structures represents a respective plurality of elements as members of a set, wherein each of the plurality of elements corresponds to a nucleic acid sub-string of the genomic reference data of the respective organism; and metadata indicating an association of each of the plurality of probabilistic data structures with a respective one of the plurality of organisms; receive data representing a nucleic acid sequence; divide the data representing the nucleic acid sequence into a plurality of portions, wherein each of the plurality of portions represents a sub-string of the nucleic acid sequence; and for each of the plurality of probabilistic data structures in the encoded genomic reference data: query the probabilistic data structure by each of the plurality of portions of the data representing the nucleic acid sequence; and generate, in response to querying the probabilistic data structure, result data comprising one or more indications of whether each of the plurality of portions of the data representing the nucleic acid sequence is a member of the set of sub-strings of the genomic reference data of the respective organism; and store the result data in a data structure comprising an indication of the organism associated with the metadata associated with the probabilistic data structure.

In some embodiments of the system, the one or more programs include instructions to, for each of the plurality of probabilistic data structures in the encoded genomic reference data, calculate a proportion of the plurality of portions of the data representing the nucleic acid sequence that are determined to be members of the set of sub-strings of the genomic reference data of the respective organism.

In some embodiments of the system, the one or more programs include instructions to, generate an output indicating the one or more organisms associated with the probabilistic data structures for which the calculated proportions are the highest among the probabilistic data structures in the encoded data.

In some embodiments of the system, generating result data comprises one of generating data indicating that an element is definitely not a member of the set and generating data indicating that an element is probably a member of the set.

In some embodiments of the system, each of the probabilistic data structures has a predefined false-positive probability.

In some embodiments of the system, the predefined false-positive probability is set at least in part in accordance with available processing resources of the one or more processors or of associated storage.

In some embodiments of the system, the predefined false-positive probability is set at least in part in accordance with available storage resources associated with the one or more processors.

In some embodiments of the system, the predefined false-positive probability is set at least in part in accordance with requirements for accuracy of comparisons to be made against the probabilistic data structure.

In some embodiments, a method for identifying genomic information in a computing environment remote from a database of genomic reference data is provided, the method comprising: at a system comprising one or more processors and a memory: receiving encoded data representing genomic reference data of a plurality of organisms, wherein the encoded data comprises: a plurality of probabilistic data structures each corresponding respectively to an organism of the plurality of organisms, wherein each of the plurality of probabilistic data structures represents a respective plurality of elements as members of a set, wherein each of the plurality of elements corresponds to a nucleic acid sub-string of the genomic reference data of the respective organism; and metadata indicating an association of each of the plurality of probabilistic data structures with a respective one of the plurality of organisms; receiving data representing a nucleic acid sequence; dividing the data representing the nucleic acid sequence into a plurality of portions, wherein each of the plurality of portions represents a sub-string of the nucleic acid sequence; and for each of the plurality of probabilistic data structures in the encoded genomic reference data: querying the probabilistic data structure by each of the plurality of portions of the data representing the nucleic acid sequence; and generating, in response to querying the probabilistic data structure, result data comprising one or more indications of whether each of the plurality of portions of the data representing the nucleic acid sequence is a member of the set of sub-strings of the genomic reference data of the respective organism; and storing the result data in a data structure comprising an indication of the organism associated with the metadata associated with the probabilistic data structure.

In some embodiments, a non-transitory computer-readable storage medium storing one or more programs for identifying genomic information in a computing environment remote from a database of genomic reference data is provided, the one or more programs configured to be executed by one or more processors and including instructions to: receive encoded data representing genomic reference data of a plurality of organisms, wherein the encoded data comprises: a plurality of probabilistic data structures each corresponding respectively to an organism of the plurality of organisms, wherein each of the plurality of probabilistic data structures represents a respective plurality of elements as members of a set, wherein each of the plurality of elements corresponds to a nucleic acid sub-string of the genomic reference data of the respective organism; and metadata indicating an association of each of the plurality of probabilistic data structures with a respective one of the plurality of organisms; receive data representing a nucleic acid sequence; divide the data representing the nucleic acid sequence into a plurality of portions, wherein each of the plurality of portions represents a sub-string of the nucleic acid sequence; and for each of the plurality of probabilistic data structures in the encoded genomic reference data: query the probabilistic data structure by each of the plurality of portions of the data representing the nucleic acid sequence; and generate, in response to querying the probabilistic data structure, result data comprising one or more indications of whether each of the plurality of portions of the data representing the nucleic acid sequence is a member of the set of sub-strings of the genomic reference data of the respective organism; and store the result data in a data structure comprising an indication of the organism associated with the metadata associated with the probabilistic data structure.

Any of the features of any of the embodiments listed above or elsewhere herein may be combined with one another.

BRIEF DESCRIPTION OF THE DRAWINGS

FIGS. 2A-2B show a flow diagram depicting a method for encoding genomic information in accordance with some embodiments.

DETAILED DESCRIPTION OF THE INVENTION

The following description sets forth exemplary methods, parameters, and the like. It should be recognized, however, that such description is not intended as a limitation on the scope of the present disclosure but is instead provided as a description of exemplary embodiments.

As explained above, traditional methods for identifying what organisms are represented by genomic data have been computationally intensive, requiring access to powerful processors, extensive computer storage, and/or high-speed network communications. There is thus a need for rapid, effective, and accurate identification of organisms represented by unidentified genomic information that can be executed without access to high-performance processors, extensive computer storage, or network communications capabilities. The systems, methods, and techniques disclosed herein, which include innovated approaches for identifying organisms such as pathogens and ABR variants using probabilistic data structures and high-speed read-mapping, may address these needs and the related needs discussed elsewhere herein.

Figure 1:
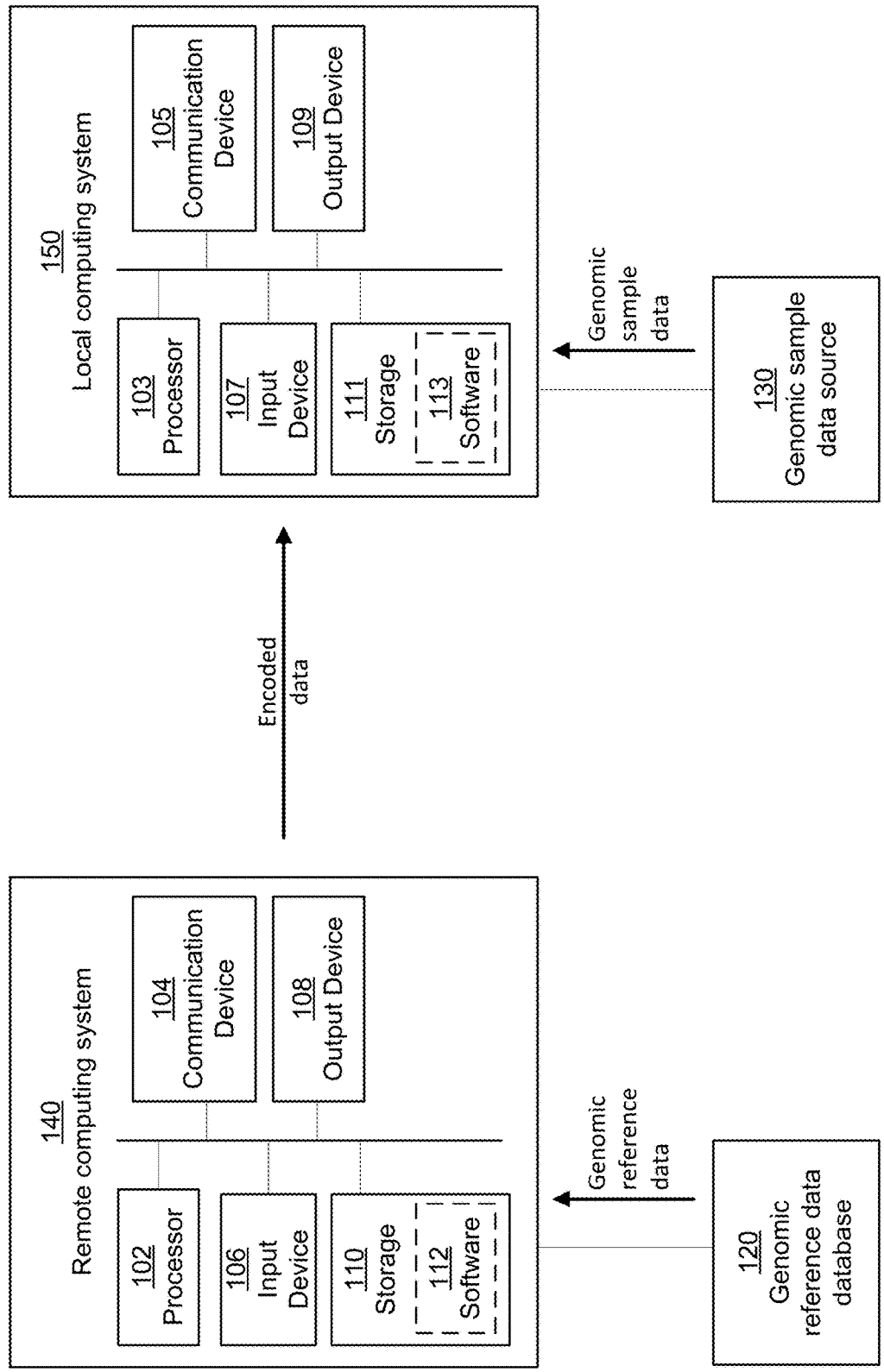
FIG. 1 shows a bioinformatics system in accordance with some embodiments.
Figure 2A:
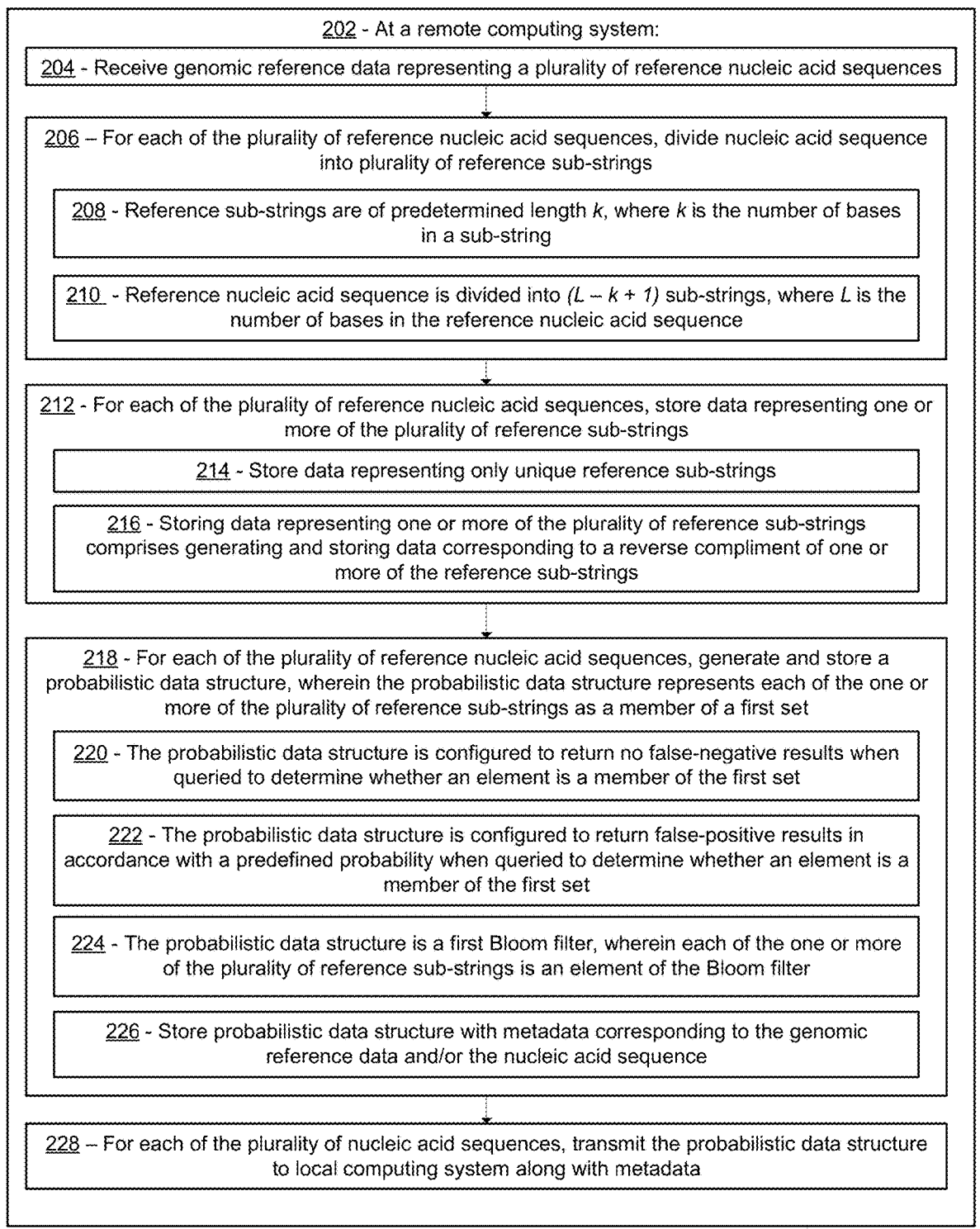

Below, FIGS. 1-2 provide a description of exemplary systems and methods for performing the techniques for rapid genomic data classification/identification using probabilistic data structures, as disclosed herein.

FIG. 1 shows bioinformatics system 100, in accordance with some embodiments, that is configured to perform one or more software processes that, when executed, provide one or more aspects of the disclosed embodiments. FIG. 1 is not intended to be limiting to the disclosed embodiment, as the components used to implement the processes and features disclosed herein may vary.

As shown in FIG. 1, in some embodiments, system 100 may comprise one or more genomic reference data databases, one or more remote computing systems, one or more local computing systems, and one or more genomic sample data sources. System 100 may be configured to process genomic information and associated metadata in order to generate one or more data structures enabling local computing systems, such as consumer-grade computing systems, to efficiently and accurately identify unknown genomic material in clinically relevant timeframes. As explained herein, using probabilistic data structures built based on information contained in the genomic reference database may enable such local computing systems to carry out said identification processes in a fast, efficient, and accurate manner.

In some embodiments, system 100 comprises genomic reference data database 120. Genomic reference data database 120 may be any computer system or server system storing identified genomic information associated with one or more organisms and/or samples. In some embodiments, genomic reference data database 120 may be any computer system or server system that is publicly and/or widely accessible via public or private electronic communication networks, storing genomic information associated with one or more organisms and/or samples. In some embodiments, genomic reference data database 120 may store WGS reference data (e.g., reference genomes) for one or more known organisms and may be accessible via the internet. For example, genomic reference data database 120 may include or be related to the National Center for Biotechnology Information (NCBI) database, the European Molecular Biology Laboratory (EMBL) database, and/or the DNA Database of Japan (DDBJ).

In some embodiments, genomic information stored in a genomic reference database may be referred to as genomic reference data, reference genomes, and/or reference sequences. In some embodiments, the genomic information and/or genomic data stored on private genomic information database 110, like genomic information and/or genomic data references elsewhere herein, may be data representing one or more nucleic acid sequences, including WGS data. Genomic reference data database 120 may store genomic information in any human-readable and/or machine-readable format, such as .fasta file format, .fastq file format, general feature format (GFF), and/or .SRA file format.

In some embodiments, the genomic reference data may comprise a plurality of representations of reference nucleic acid sequences, wherein metadata associates each of the plurality of reference nucleic acid sequences with a known species, organism, and/or strain.

In some embodiments, genomic reference data database 120 may store genomic reference data associated with one or more organisms along with metadata. In some embodiments, metadata may include data relating to an identity of an organism, species, and/or strain. In some embodiments, other metadata may be stored in association with reference data; other metadata may relate to reference data and/or to samples from which the reference data was originally derived. For example, other metadata may be related to one or more associated parties or organizations; one or more data sources; location information and/or time information at which a sample was taken or reference data was identified; a type of a sample; a quality of a sample; a manner in which a sample was collected; a party that collected a sample; a manner in which (and parties by which) a sample was transported; locations and/or routes along which a sample was transported, including times at which the sample was present at various locations; confidentiality metadata indicating a confidentiality level of a sample and/or of an associated party; genomic information that is known or suspected about a sample before sequencing and/or before post-sequencing bioinformatics processing, such as a known or suspected organism, known or suspected serovar, or other known or suspected genomic information; a time at which a sample was located at one or more facilities or locations; personnel that came into contact with the sample at various times; and/or a transportation service associated with a sample. In some embodiments, some or all metadata may be fully or partially anonymized before or after receipt by system 100.

In some embodiments, system 100 comprises genomic sample data source 130. In some embodiments, genomic sample data source 130 may share some or all properties in common with genomic reference data database 120 as discussed above, except that one or more genomic data element stored on or associated with genomic sample data source 130 may be unidentified. That is, some genomic data from genomic sample data source 130 may not yet be associated with metadata identifying the genomic information that it represents, and users of the system may therefore not be aware of what organisms, species, and/or strains are represented by the unidentified genomic data. In some embodiments, the genomic data stored and/or provided by on genomic sample data source 130 may be referred to as sample data, query data, unidentified data, unclassified data, and/or read-set data.

In some embodiments, genomic sample data source 130 may be any computer storage (e.g., memory or disk storage) or database, or it may be any other electronic device configured to generate, store, and/or transmit data representing genomic data such as read-set including one or more nucleic acid sequences. Publically available read-set data may be accessed through the NCBI-SRA data base. Data that is found in the NCBI-SRA database may come from sequencing laboratories. These laboratories may use sequencing machines such as Illumina, PacBio, Roche 454, and/or MinIon to produce read-sets from clinical/nonclinical samples. In some embodiments, read-set data may be produced by portable sequencers applicable in field applications. In some embodiments, while genomic reference data database 120 may be in electronic communication with one or more communication networks (such as the internet), genomic sample data source 130 may not be configured for network communication or for high-speed or wide-area network communication. In some embodiments, genomic sample data source 130 may be exclusively or non-exclusively associated with one or more corporations, educational institutions, laboratories, government entities, medical facilities, military facilities, packaging facilities, processing facilities, factories, distribution facilities, shipping terminals, warehouses, transportation hubs, stores, markets, restaurants, farms, ranches, slaughterhouses, and/or any other private or public institutions.

Genomic sample data source 130 may store genomic information in any human-readable and/or machine-readable format, such as .fasta file format, .fastq file format, general feature format (GFF), and/or .SRA file format. In some embodiments, the genomic information and/or genomic data stored and/or provided by genomic sample data source 130, like genomic information and/or genomic data references elsewhere herein, may be data representing one or more nucleic acid sequences, such as genomic read-sets.

In some embodiments, genomic sample data source 130 may store genomic information associated with one or more organisms and/or samples along with metadata. In some embodiments, metadata may include data relating to an identity (whether known or presumed with various levels of confidence) of an organism associated with a sample; one or more associated parties or organizations; one or more data sources; location information and/or time information at which a sample was taken; a type of a sample; a manner in which a sample was collected; a party that collected a sample; a manner in which (and parties by which) a sample was transported; locations and/or routes along which a sample was transported, including times at which the sample was present at various locations; confidentiality metadata indicating a confidentiality level of a sample and/or of an associated party; genomic information that is known or suspected about a sample before sequencing and/or before post-sequencing bioinformatics processing, such as a known or suspected organism, known or suspected serovar, or other known or suspected genomic information; a time at which a sample was located at one or more facilities or locations; personnel that came into contact with the sample at various times; and/or a transportation service associated with a sample.

In some embodiments, system 100 may comprise remote computing system 140, which may be any computer configured to receive, process, analyze and store genomic data as described further herein. As described in detail herein (and as shown in FIG. 1), remote computing system 140 may be configured, in some embodiments, to receive genomic reference data from genomic reference data database 120; to use the genomic reference data received to create encoded/compressed data comprising a plurality of probabilistic data structures, each representing an identified nucleic acid sequence of the genomic reference data; and to transfer the encoded data to local computing system 150.

In some embodiments, the genomic information stored in genomic reference data database 120, storage 110, or elsewhere on or in association with system 100 may be in a format configured to be applied to an index, for example as described in U.S. patent application Ser. No. 15/337,754, titled "Food Pathogen Bioinformatics," which is hereby incorporated by reference in its entirety. In some embodiments, the information is compressed information, such as any of the compressed information described in U.S. patent application Ser. No. 14/718,950, titled "Compression and Transmission of Genomic Information," which is hereby incorporated by reference in its entirety. In some embodiments, any computer storage on or associated with system 100 may include a stored generalized index such that compressed genomic information may be applied against the generalized index to be decompressed, such as described in U.S. patent application Ser. No. 14/718,950, as may be required.

Remote computing system 140 can be any suitable type of microprocessor-based device, such as a personal computer; workstation; server; handheld computing device, such as a phone or tablet; or distributed computing system (e.g., cloud computing system). The system can include, for example, one or more of processor 102, communication device 104, input device 106, output device 108, storage 110, and/or software 112 stored on storage 110 and executable by processor 102. The components of the computing system 130 can be connected in any suitable manner, such as via one or more physical buses or wirelessly.

In some embodiments, remote computing system 140 may include server-side computing components as well as client-side computing components. The specific elements shown in FIG. 1 may, in some embodiments, be included in a server-side computer and/or may, in some embodiments, be included in a client-side computer. In some embodiments, remote computing system 140 may include server-side components and client-side components that are in communication with one another via one or more instances of communication device 104, which may, for example, enable communication of server-side components and client-side components over a network connection.

In some embodiments, some or all components of remote computing system 140 may be part of a distributed computing system (e.g., a cloud computing system). In some embodiments of the techniques disclosed herein, for example, storage 110 may be storage provisioned by a cloud computing system, such that a user may send instructions to the cloud computing system over one or more network connections, and the cloud computing system may execute the instructions in order to leverage the cloud computing components in accordance with the instructions. In some embodiments, cloud computing systems may be configured to be capable of executing the same or similar program code in the same programming languages as other systems (e.g., servers, personal computers, laptops, etc.) as discussed herein.

Processor 102 may be any suitable type of computer processor capable of communicating with the other components of remote computing system 140 in order to execute computer-readable instructions and to cause remote computing system 140 to carry out actions in accordance with the instructions. For example, processor 100 may access a computer program (e.g., software 112) that may be stored on storage 110 and execute the program to cause the system to perform various actions in accordance with the program. In some embodiments, a computer program or other instructions executed by processor 102 may be stored on any transitory or non-transitory computer-readable storage medium readable by processor 102.

In some embodiments, processor 102 may include one or more known processing devices, such as a microprocessor from the Pentium™ family manufactured by Intel™ or the Turion™ family manufactured by AMD™. Processor 102 may include a single core or multiple core processor system that provides the ability to perform parallel processes simultaneously. For example, processing unit 111a may include a single core processor that is configured with virtual processing technologies known to those skilled in the art. In certain embodiments, processor 102 may use logical processors to simultaneously execute and control multiple processes. The one or more processors in processor 102 may implement virtual machine technologies or other similar known technologies to provide the ability to execute, control, run, manipulate, store, etc.; multiple software processes; applications; programs; etc. In another embodiment, processor 102 may include a multiple-core processor arrangement (e.g., dual or quad core) that is configured to provide parallel processing functionalities to allow remote computing system 140 to execute multiple processes simultaneously. Other types of processor arrangements, such as those used in Cray supercomputers, could be implemented to provide for the capabilities disclosed herein.

Communication device 104 may include any suitable device capable of transmitting and receiving signals over a network, such as a network interface chip or card. Remote computing system 140 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Input device 106 may be any suitable device that provides input, such as a touch screen or monitor, keyboard, mouse, button or key or other actuatable input mechanism, microphone, and/or voice-recognition device, gyroscope, camera, or IR sensor. Output device 108 may be any suitable device that provides output, such as a touch screen, monitor, printer, disk drive, light, speaker, or haptic output device. Input device 106 and/or output device 108 may include components configured to send and/or receive information between components of remote computing system 140 or external to remote computing system 140.

Storage 110 can be any suitable device that provides storage, such as an electrical, magnetic, or optical memory including a RAM, cache, hard drive, CD-ROM drive, tape drive, or removable storage disk. In some embodiments, storage 110 may include instructions that, when executed by one or more processors of processor 102, perform one or more processes consistent with the functionalities disclosed herein. Storage 110 may also include any combination of one or more databases controlled by memory controller devices (e.g., server(s), etc.) or software, such as document management systems, Microsoft SQL databases, SharePoint databases, Oracle™ databases, Sybase™ databases, or other relational databases. In some embodiments, storage 110 may contain or be communicatively coupled to any one or more of the databases discussed herein.

In some embodiments, instructions, application programs, etc. may be stored in an external storage or available from a memory over a public or private network to which remote computing system 140 is communicatively coupled. The one or more processors in processor 102 may execute one or more programs located remotely from remote computing system 140 and/or system 100. For example, remote computing system 140 may access one or more remote programs, that, when executed, perform functions related to disclosed embodiments. Storage 110 may include one or more memory devices that store data and instructions used to perform one or more features of the disclosed embodiments.

Software 112, which may be stored in storage 110 and executed by processor 102, may include, for example, the programming that embodies the functionality of the methods, techniques, and other aspects of the present disclosure (e.g., as embodied in the computers, servers, and devices as described above). In some embodiments, software 112 may include a combination of servers such as application servers and database servers.

Methods, systems, and articles of manufacture consistent with disclosed embodiments are not limited to separate programs or computers configured to perform dedicated tasks. For example, remote computing system 140 may include storage that may include one or more programs to perform one or more functions for encoding, compressing, and/or anonymizing genomic information by way of probabilistic data structures and/or performing comparisons or other analytics on the probabilistic data structures.

Software 112 can also be stored and/or transported within any computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 110, that can contain or store programming for use by or in connection with an instruction execution system, apparatus, or device.

Software 112 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

Remote computing system 140 can implement any one or more operating systems suitable for operating on the network. Software 112 can be written in any one or more suitable programming languages, such as C, C++, Java, or Python. In various embodiments, application software embodying the functionality of the present disclosure can be deployed in different configurations, such as in a client/server arrangement or through a Web browser as a Web-based application or Web service, for example.

In some embodiments, genomic reference data database 120 may be communicatively coupled by a public or private electronic communication network with remote computing system 140. Remote computing system 140 may be communicatively connected to one or more memory devices (e.g., databases (including but not limited to private database 112 and public database 114)) locally or through a public or private network. The remote memory devices may be configured to store information and may be accessed and/or managed by remote computing system 140. By way of example, the remote memory devices may be document management systems, Microsoft SQL databases, SharePoint databases, Oracle™ databases, Sybase™ databases, or other relational databases. Systems and methods of disclosed embodiments, however, are not limited to separate databases or even to the use of a database.

In some embodiments, remote computing system 140 may create, receive, store, and/or provide one or more indexes of a nucleic acid sequence or an amino acid sequence. Any such index may include a plurality of elements, with each element corresponding to a permutation of a nucleic acid sequence or an amino acid sequence (or another type of sequence). Remote computing system 140 may implement the index using a variety of data structures, such as databases, matrices, arrays, linked lists, trees, and the like. The choice of data structures may vary. Remote computing system 140 may store the index in storage 110 and/or in one or more associated databases. More specifically, the index may be stored on hard disk; remote computing system 140 may also load the index into RAM for increased performance.

In some embodiments, remote computing system 140 may create, receive, store, and/or provide one or more probabilistic data structures. Any such probabilistic data structures may include, represent, or correspond to one or more elements included in a data set. In some embodiments, any such probabilistic data structure may be created based on genomic information, wherein one or more strings, substrings, or other characteristics of genomic information and/or associated metadata may be an element represented as part of a set by a probabilistic data structure. Remote computing system 140 may store the probabilistic data structure in storage 110 and/or in one or more associated databases. More specifically, the probabilistic data structure may be stored on hard disk; remote computing system 140 may also load the probabilistic data structure into RAM for increased performance.

In some embodiments, system 100 may comprise local computing system 150, which may be any computer configured to receive, process, analyze and store genomic data as described further herein. As described in detail herein (and as shown in FIG. 1), local computing system 150 may be configured to receive, from remote computing system 140, encoded/compressed data comprising a plurality of probabilistic data structures, each representing an identified nucleic acid sequence of genomic reference data; to receive genomic unidentified/unclassified sample data (e.g., input/query/sample read-set data) from genomic sample data source 130; and to use the probabilistic data structures and encoded/compressed data to identify one or more organisms, species, and/or strains associated with the previously unidentified genomic sample data.

Local computing system 150 may share in common with remote computing system 140 any one or more of the elements and/or properties discussed above. While remote computing system 140 may comprise one or more of processor 102, communication device 104, input device 106, output device 108, storage 110, and/or software 112 stored on storage 110 and executable by processor 102, local computing system 150 may comprise one or more of processor 103, communication device 105, input device 107, output device 109, storage 111, and/or software 113 stored on storage 111 and executable by processor 103. The components of the local computing system 150 can be connected in any suitable manner, such as via one or more physical buses or wirelessly. In some embodiments, rather than being communicatively coupled by a public or private electronic communication network with genomic reference data database 120, computing system 140 may be similarly communicatively coupled with genomic sample data source 130.

In some embodiments, remote computing system 140 may have greater computational, processing, storage, memory, and/or communication capabilities than local computing system 150. In some embodiments, remote computing system 140 may comprise one or more supercomputers and/or cloud computing servers, whereas local computing system 150 may comprise one or more consumer-grade computing devices such as a personal computer, laptop, tablet, smart-phone, and/or a single-board computer. In some embodiments, remote computing system 140 may have one or more network connections such as internet access, high-speed data upload and/or download capabilities, and/or cloud computing access; whereas local computing system 150 may have inferior network connection and/or communication capabilities, such as slower data rates for uploads and/or downloads, restricted network access, or no network access.

In some embodiments, remote computing system 140 and local computing system 150 may be communicatively coupled with one another by a public or private electronic communication network. In some embodiments, the communicative link between the two may be limited by the communication capabilities of local computing system 150, which may be inferior to the communication capabilities of remote computing system 140. In some embodiments, the communicative link between the two may only exist intermittently, such that the encoded data may be transferred when the link is active, and the link may then be thereafter severed. As explained below, local computing system 150 may then carry out genomic data identification and analysis without reliance on the communicative link to remote computing system 140 and/or genomic reference data database 120.

FIG. 2 depicts a method for processing, storing, analyzing, and identifying genomic information via probabilistic data structures, in accordance with some embodiments. The method 200 may be performed by a system such as the system 100 described above with reference to FIG. 1. In the described embodiments, certain method steps are performed by certain elements and/or certain parties or by certain system components; however, in other embodiments, each of the method steps may be performed by any of the other elements and/or parties described herein, or the elements and/or parties performing each step may be associated with one another, may be a related element and/or party, or may be the same element and/or party.

As will be described below, the methods described herein, including exemplary method 200, may enable fast, efficient, accurate, precise, and secure analysis and identification/classification of unknown genetic material, without the need for extensive computational, storage, or communication resources or capabilities and in clinically meaningful timeframes. The methods described herein may thus enable the rapid identification of unknown genomic data by identifying the most likely matches from among thousands, tens of thousands, hundreds of thousands, or more reference genomic data samples, and may enable performing this identification on consumer-grade computing devices (e.g., laptops, smart phones, or single-board computers) within a matter of hours, minutes, or seconds per sample.

At block 202, in some embodiments, blocks 204-228 may represent steps performed at a remote computing system. In some embodiments, a remote computing system may refer to any computing system distinct from a local computing system, as defined with physical and/or communicative (e.g., network) proximity to any one or more users or computing components. In some embodiments, a remote computing system may refer to any first computing system distinct from any second computing system. In the example of system 100 of FIG. 1, the remote computing system may be remote computing system 140 (while the local computing system discussed below may be local computing system 150).

At block 204, in some embodiments, genomic reference data representing a plurality of reference nucleic acid sequences may be received. In some embodiments, a reference nucleic acid sequence may be any nucleic acid sequence for which associated metadata, such as metadata identifying a corresponding organism, species, and/or strain, is known. In some embodiments, the genomic reference data may include WGS data identified as being associated with a specific organism and may be stored along with metadata identifying the reference data as the specific organism (e.g., a specific genus, species, strain, serovar, etc.). In some embodiments, genomic reference data may be whole genome sequencing data.

In some embodiments, genomic reference data may be received by one or more computers configured to store, analyze, process, encode, and/or transmit the genomic reference data. In the example of system 100 of FIG. 1, genomic reference data may be received by remote computing system 140 from genomic reference data database 120. In some embodiments, the genomic reference data may be received in association with metadata, including metadata identifying an organism represented by the genomic reference data and/or including any of the metadata discussed above with respect to genomic reference data database 120 in FIG. 1.

At block 206, in some embodiments, for each of the plurality of reference nucleic acid sequences, the nucleic acid sequence may be divided into a plurality of reference sub-strings. In the example of system 100 in FIG. 1, remote computing system 140 may divide each of the plurality of nucleic acid sequences received from genomic reference data database 120 into a plurality of sub-strings having a shorter length than the original respective nucleic acid sequence. In some embodiments, this division may be performed concurrently with respect to two or more of the plurality of nucleic acid sequences, while in some embodiments the plurality of nucleic acid sequences may be divided one at a time. In either event, the division may yield, for each of the nucleic acid sequences, a respective plurality of reference sub-strings that may be found in the overall nucleic acid sequence at one or more locations.

At block 208, in some embodiments, the reference sub-strings may be of predetermined length k, where k is the number of bases in a sub-string. At block 210, in some embodiments, the reference nucleic acid sequence may be divided into (L−k+1) sub-strings, where L is the number of bases in the reference nucleic acid sequence.

In some embodiments, the process of dividing a string of genomic data into a plurality of sub-strings may be referred to as "k-merizing" the string of genomic data, in that each of the sub-strings into which the string is divided may be referred to as a k-mer. In some embodiments, the specific number to which k is set may be used to refer to the k-mer; for example, if k is equal to 16, then the k-mer may be referred to as a 16-mer, and if k is equal to 12, then the k-mer may be referred to as a 12-mer. By selecting a predetermined length k, and dividing an overall string of genomic information into sub-strings of length k by shifting down the string by one base per iteration, the overall string may be k-merized into (L−k+1) sub-strings or k-mers of length k.

In some embodiments, the length k may be selected based on requirements of the specific application. For example, a challenge in implementation of the techniques described herein may be the presence of mutations and SNPs in the genomic sample data (see below). Since probabilistic data structures may require exact string matches when testing for a match, a SNP or mutation may result in a result being returned that indicates no match due to a single (and perhaps inconsequential) SNP. In some embodiments, in light of these considerations, statistical analysis may be used to determine the optimal k-mer length; if a k-mer is too short, it becomes too generic and will be found in too many different reference nucleic acid sequences; if it is too long, the probability of a mutation or SNP preventing detection of a match increases. In some embodiments, alternately or additionally, a suite of probabilistic data structures of varying k-mer lengths for each organism (e.g., for each reference nucleic acid sequence) may be used, which may allow for finding consensus across multiple k-mer lengths.

In some embodiments, the k-merization process may be applied to one or more strings of genomic information from the genomic reference data (e.g., WGS data) and also to one or more strings of unidentified genomic data (e.g., a read set), as discussed further below. In some embodiments, the length k used for the k-merization of both types of data, and for the k-merization of multiple nucleic acid sequences in the same body of genomic reference data, may be the same, such that all resulting sub-strings may have the same length. In some embodiments, by k-merizing different strings of genomic data using the same length k, different numbers of k-mers may be generated for the different strings. For example, if a WGS data nucleic acid sequence included in the genomic reference data has a longer length L than a string in an unidentified read-set, then more reference sub-strings may be generated than sub-strings for the read-set (e.g., query sub-strings, as discussed further below). In some embodiments, such as where L is equivalent for two different genomic strings, the number of sub-strings resulting from each string may be the same.

At block 212, in some embodiments, for each of the plurality of reference nucleic acid sequences, data representing one or more of the plurality of reference sub-strings may be stored. In some embodiments, the data representing one or more of the plurality of reference sub-strings may be stored or represented using a hashmap in association with WGS data and/or .fasta or .fastq file formats. In some embodiments, all of the reference sub-strings may be stored in a database and/or other computer storage or memory associated with the system. In the example of system 100 of FIG. 1, the one or more of the plurality of reference sub-strings may be stored in storage 110. In some embodiments, the one or more sub-strings may be stored along with metadata, such as metadata identifying the nucleic acid sequence (e.g., the overall string) to which the sub-string corresponds and/or metadata identifying a source, organism, and/or sample associated with the genomic information. Thus, by storing the reference sub-strings along with metadata identifying source information, a system and/or user may be able to look up individual sub-strings to determine which sub-strings correspond to which original nucleic acid sequence or genomic information.

In some embodiments, metadata indicating a location of a reference sub-string in the original reference nucleic acid sequence may be stored in association the respective reference sub-string, while in some embodiments no such location data may be stored.

At block 214, in some embodiments, data representing only unique reference sub-strings may be stored. Thus, storing data representing one or more of the plurality of reference sub-strings may comprise storing data representing only unique reference sub-strings when compared with the other reference sub-strings attributable to the reference nucleic acid sequence. For example, a system may only store data once for each sub-string that is determined to appear in a nucleic acid sequence, instead of storing multiple data elements in the event that the same sub-string appears two or more times in different locations in the same nucleic acid sequence.

For example, in embodiments in which the sub-strings themselves are stored, a system may store only one copy of each unique sub-string per nucleic acid sequence, rather than storing multiple copies of sub-strings that appear more than once in the same nucleic acid sequence. Thus, rather than storing an exhaustive list of each k-mer of length k that appears at each and every position of a nucleic acid sequence, a system may instead compile a list or stored record that comprises or represents all unique k-mers (for each nucleic acid sequence) that appear in the nucleic acid sequence. In some embodiments, this record of unique k-mers may be stored as a list of each unique k-mer, as a plurality of pointers to an index in which each unique k-mer may be looked up, or in any other suitable format. By storing only data corresponding to unique k-mers for each nucleic acid sequence, and not to each and every k-mer appearing in genetic data, computational and storage resources may both be conserved, while the look-up functions discussed further below may not be compromised.

In some embodiments, despite only storing unique sub-strings or only storing one record of each unique sub-string, an associated record or other indication may also be stored indicating how many times each unique sub-string is encountered in the data.

At block 216, in some embodiments, storing data representing one or more of the plurality of reference sub-strings comprises generating and storing data corresponding to a reverse compliment of one or more of the reference sub-strings. Because sequenced genomic data corresponding to the same portion of the same genome of the same organism may be sequenced either as a first sequence of bases or as the reverse complement (e.g., a reverse complement of a sequence of DNA is formed by interchanging A and T, interchanging C and G, and then reversing the order) of that series of bases (e.g., ATTCGG becomes CCGAAT), calculating a reverse complement of sub-strings from a read-set and/or from sequenced genomic data and/or WGS data may be important when comparing sub-strings from different data sources to look for matching sub-strings. This may eliminate potential redundancy and inaccuracy introduced by the uncertainty of whether a sequence is 3-5 prime or 5-3 prime. If reverse complements are not calculated and included in lists or indexes or sub-strings, then reverse-complement sub-strings that may be indicative of a common species or common organism may evade detection. (In some embodiments, a system could store both a string and its reverse compliment, which may allow look-up to be performed without normalization of query data; however, it could require more space for storage.)

Thus, in some embodiments, when compiling a list, index, or other stored data structure indicating all unique sub-strings associated with a sequence of genomic information, a system may also calculate all reverse complements of all sub-strings in that sequence and may store an indication only of one sub-string of a reverse complement pair of two sub-strings. For example, data representing the string ATTCGG may be stored, while data representing CCGAAT (its reverse complement) may not be additionally stored with reference to the same genetic data. A user or system may select any suitable convention to determine which string of reverse complement pairs is retained and which string is discarded.

At block 218, in some embodiments, for each of the plurality of reference nucleic acid sequences, a probabilistic data structure may be generated and stored, wherein the probabilistic data structure represents each of the one or more of the plurality of reference sub-strings as a member of a first set. In some embodiments, after the reference genomic data has been divided into reference sub-strings, and after data corresponding to one or more of the reference sub-strings has been stored, a system may generate, for each of the reference nucleic acid sequences, a respective probabilistic data structure representing each of the one or more reference sub-strings in the respective reference nucleic acid sequence. For example, if a reference nucleic acid sequence is k-merized and 100 unique sensitive k-mers are identified and stored in association with the reference nucleic acid sequence, then a probabilistic data structure may be generated and stored that represents each of the 100 unique sensitive k-mers as members of a set.

This may be done for each reference nucleic acid sequence in a database or library of reference genomic data, which may yield thousands, tens of thousands, or hundreds of thousands or more probabilistic data structures, each corresponding to an individual reference nucleic acid sequence. In some embodiments, this process may be computationally intensive, especially for a large body of genomic reference data containing many reference nucleic acid sequences.

In some embodiments, the probabilistic data structure may be generated by any suitable processor acting on data representing the one or more of the plurality of reference sub-strings, and the probabilistic data structure may be built and stored on any suitable computer storage, computer memory, and/or database, or may be transmitted thereto for storage. In some embodiments, creation of the plurality of nucleic acid sequences may be carried out by a high-performance computing system such as a supercomputer or a distributed computing system. In the example of system 100 of FIG. 1, remote computing system 140 may create the plurality of probabilistic data structures by performing one or more calculations and operations against stored data representing the reference sub-strings and may store the probabilistic data structures on storage 110.

In some embodiments, the probabilistic data structure may be configured such that the data elements used to create the probabilistic data structure (e.g., the data upon which the probabilistic data structure was based or the input data used in the creation of the probabilistic data structure) may be unrecoverable from the probabilistic data structure. For example, the probabilistic data structure may comprise a one-way encoding algorithm that prevents the original elements from being recovered based on the probabilistic data structure. In some embodiments, the data elements may be unrecoverable due to an extremely intensive and/or computationally infeasible calculation or calculations that would be required to reverse the encoding and recover the elements. In some embodiments, the data elements may be unrecoverable in that reversal of the encoding may generate additional data elements that were not used in the creation or building of the probabilistic data structure, wherein those additional data elements may be indistinguishable from the data elements on which the probabilistic data structure was actually based; in this way, a party that reverses the encoding/compression process used in the creation of the probabilistic data structure to produce various data elements from the probabilistic data structure may not know which produced data elements were actually used to create the probabilistic data structure and which produced data elements are random, modified, and/or spoof data elements.

At block 220, in some embodiments, the probabilistic data structure is configured to return no false negative results when queried to determine whether an element is a member of the first set. At block 222, in some embodiments, the probabilistic data structure is configured to return false-positive results in accordance with a predefined probability when queried to determine whether an element is a member of the first set.

In some embodiments, a probabilistic data structure that returns no false negative results and a predefined and/or user-definable percentage of false positive results may have useful applications in genomic data analytics, in that it may allow for a rapid and effective comparison of known data against the probabilistic data structure to quickly determine, with a known error rate, whether the known data is probably included in the data set or whether the known data is definitely not included in the data set. In some embodiments, such as bioinformatics applications in which genomic data may need to be compared to large amounts of reference data (e.g., millions of data elements or more), a small error rate in the form of false positive results may be acceptable, in that useful comparative results may still be generated. For example, comparative results may be generated that show a known organism or species with the highest similarity to genomic information of a test sample, and this result may be able to be generated substantially more quickly than if an exhaustive and error-free comparison were made.

Furthermore, in some embodiments, using a probabilistic data structure that returns no false negative results and a predefined and/or user-definable percentage of false positive results may conserve storage space, as the probabilistic data structure may be substantially smaller in size than an exhaustive list or other error-free data structure representing all of the data elements of the set. In some embodiments, a the estimated size of a Bloom filter may be calculated based on the number of elements and the false positive rate selected, while the size of the input itself may not matter to the calculation of that size. In one example, a body of more than 7,000 nucleic acid sequences representing WGS data for bacteria may be represented, along with associated metadata, as probabilistic data structures totaling less than 8 GB in disk storage space.

In some embodiments, using a probabilistic data structure that returns no false negative results and a predefined and/or user-definable percentage of false positive results may allow for sensitive genomic information to be disclosed safely and without undue risk that an associated party may be determined to be definitively associated with the sensitive genomic information. This is discussed extensively in U.S. Provisional Patent Application No. 62/505,376, filed May 12, 2017, titled "Secure Communication of Sensitive Genomic Information Using Probabilistic Data Structures," which is hereby incorporated in its entirety.

In some embodiments, the false positive probability of the probabilistic data structure may be selectable by a user or a system, such that a false positive probability may be selected and set and used in the creation of the probabilistic data structure. For example, a user may choose to create a probabilistic data structure configured to return false positive results at any suitable rate, such as 0.1%, 0.5%, 1%, 2%, 5%, 10%, 20%, 25%, 30%, 40%, or 45%. In some embodiments, a probabilistic data structure may be configured to return false positive results at a rate of 50% or more.

In some embodiments, the false positive probability may be selected based at least in part on storage and/or computing resources. For example, the lower the false positive probability, the more storage space may be required to store the probabilistic data structure and the more computational resources may be required to create/build the probabilistic data structure.

In some embodiments, the false positive probability may be selected based at least in part on requirements or considerations for accuracy and precision of comparisons to be made against the probabilistic data structure. For example, in some applications, such as those in which data sets for comparison are smaller, then higher false positive rates may degrade results substantially and unacceptably. However, in some applications, such as those in which data sets for comparison are larger (e.g., hundreds, thousands, or millions of elements to compare), then higher false positive rates may be acceptable as they may not impede the ability to draw meaningful conclusions (e.g., what organism is most likely represented by the k-mers used to build this probabilistic data structure?) from analysis of the probabilistic data structure.

At block 224, in some embodiments, the probabilistic data structure is a first Bloom filter, wherein each of the one or more of the plurality of reference sub-strings is an element of the Bloom filter.

In some embodiments, a probabilistic data structure used for encoding and compressing genomic information may be a Bloom filter. A Bloom filter is a probabilistic data structure that may be used to determine whether an element is a member of a set. Unlike a set or traditional database, the data in a Bloom filter is irretrievable. When a Bloom filter is queried as to whether an element is a member of a set, the Bloom filter will provide zero false negative results, but may provide false positive results. Thus, a Bloom filter may be used to determine whether an element is "probably present" or "definitely not present" in a set. The rate at which false positive results are returned may be selected by a user at the time of the creation of a Bloom filter, such that a Bloom filter may be configured to have a predetermined probability of returning false positive results. The false positive rate of a Bloom filter is pre-defined with a correlation to the number of elements to be added to the filter. For example, a Bloom filter may be configured to return false positive results 40%, 30%, 20%, 10%, 5%, 2%, 1%, or less than 1% of the time.

Bloom filters are space-efficient, in that they require less disk space for storage and memory for comparison processes than error-free (e.g., 0% false positive) hashing techniques or other data structures for representing and searching sets (e.g., search trees, hash tables, arrays, or linked lists). In some embodiments, a Bloom filter having a 1% false positive probability may require less than 10 bits per element represented by the Bloom filter. The lower a false positive probability is set, the larger the Bloom filter data structure will be; the higher the false positive probability, the smaller the Bloom filter data structure will be.

A Bloom filter gets the zero false negative rate by virtue of how data is inserted and looked up. Upon insertion, each data point is hashed and converted into two or more bit positions. These bits are then set to true (1) within the bit array. It is possible that multiple data points overlap on one or more bits. When looking up a data point to see if it has been included, the data to be looked up is hashed in the same manner used to hash the original data. All bits are checked to verify that they are all set. If any bit is not set to true, one can be confident that the data point was never inserted.

In some embodiments, creating the probabilistic data structure may comprise building a Bloom filter, which may be carried out by remote computing system 140 in the example of system 100 of FIG. 1. In some embodiments, a Bloom filter may be created for each reference nucleic acid sequence in the genomic reference data by using each of the plurality of reference sub-strings from a respective reference nucleic acid sequence (e.g., the k-mers extracted from a respective reference nucleic acid sequence) as an element for the creation of a Bloom filter. In some embodiments, a system may be configured to allow for parallel building, exporting and importing from disk, and importing and exporting in several file formats including hex strings of Bloom filters, binary, and reading directly from disk instead of loading into memory. In some embodiments, a system may enable storing statistics about a Bloom filter including the number of elements stored, desired false positive rate, and/or the maximum number of elements to stay below that false positive rate. Thus, for a system having access to a library of thousands or tens of thousands of reference nucleic acid sequences, thousands or tens of thousands of respective Bloom filters may be created, one to represent each reference nucleic acid sequence.

At block 226, in some embodiments, the probabilistic data structure may be stored with metadata corresponding to the genomic reference data and/or the nucleic acid sequence. In some embodiments, each of the plurality of probabilistic data structures created to represent respective reference nucleic acid sequences may be stored separately and/or together on any suitable computer storage, such as storage 110.

In some embodiments, each probabilistic data structure (or some of the probabilistic data structures) may be stored in association with metadata, which may include any of the metadata discussed above regarding to the reference genomic data. Metadata may include any metadata indicating an identity of one or more organisms represented by the data and/or include any metadata indicating one or more parties associated with the sensitive genomic information. In some embodiments, the probabilistic data structures may be stored as part of an index, library, or database of thousands, tens of thousands, or hundreds of thousands or more probabilistic data structures representing various nucleic acid sequences, and identify metadata stored along with each probabilistic data structure may allow systems and/or users to identify which probabilistic data structures correspond to which nucleic acid sequences (e.g., what organism, species, strain, etc.).

At block 228, in some embodiments, for each of the plurality of nucleic acid sequences, the probabilistic data structure may be transmitted to a local computing system along with metadata. In some embodiments, one or more probabilistic data structures may be transferred from a remote computing system to a local computing system via any electronic communication link, such as any suitable network communication link.

In some embodiments, the plurality of probabilistic data structures may be transmitted along with metadata allowing identification and/or indexing of the probabilistic data structures, such that a library or index of probabilistic data structures is transferred. In some embodiments, probabilistic data structures may be transferred one at a time or in one or more batches each including two or more probabilistic data structures. In some embodiments, an entire library of hundreds of thousands or more probabilistic data structures may be transferred at once. In some embodiments, such as when the plurality of probabilistic data structures constitute a large file size, the plurality of probabilistic data structures may be transferred by physical media, such as being transferred on one or more discs, thumb drives, hard drives, solid-state drives, or the like. For example, if the plurality of probabilistic data structures amount to several gigabytes in total size for several thousand probabilistic data structures, then the probabilistic data structures may be loaded onto portable storage media (or alternately transmitted by network communication) and then transferred to the local computing system. This transfer may, in some embodiments, be made on a one-time or periodic basis, such that the local computing system may then perform the analyses discussed below without further need for communication with the remote computing system, thereby enabling genomic analysis to be performed in various scenarios in which network communication capabilities and/or computing resources are limited (e.g., to consumer-grade, non-network-connected computers).

At block 230, in some embodiments, blocks 232-254 may represent steps performed at a local computing system. In some embodiments, a local computing system may refer to any computing system distinct from a remote computing system, as defined with physical and/or communicative (e.g., network) proximity to any one or more users or computing components. In some embodiments, a local computing system may refer to any first computing system distinct from any second computing system. In the example of system 100 of FIG. 1, the local computing system may be local computing system 150.

At block 232, in some embodiments, the plurality of probabilistic data structures and metadata may be received from the remote computing system. In some embodiments, the local computing system may receive the plurality of probabilistic data structures and accompanying metadata in accordance with any of the techniques discussed above with respect to transferring the probabilistic data structures and associated metadata from the remote computing system. In the example of system 100 of FIG. 1, local computing system 150 may receive the plurality of probabilistic data structures and associated metadata from remote computing system 140.

At block 234, in some embodiments, query data representing one or more query nucleic acid sequences may be received. In some embodiments, query data may be alternately referred to as genomic sample data and may comprise any data that is intended to be compared against reference genomic information, probabilistic data structures, libraries, indexes, or keys; query data may comprise unidentified nucleic acid sequences that have not yet been determined to be associated with one or more known organisms, species, or strains. In some embodiments, the query data may comprise one or more read-sets including one or more unidentified nucleic acid sequences, which may be received from internal and/or external laboratories and may be generated by using genetic sequencers. In some embodiments, as discussed below, the query data may be used to query one or more probabilistic data structures, libraries, indexes, or keys in order to identify the one or more query nucleic acid sequences.

In some embodiments, query data may be received by one or more computers configured to store, analyze, process, encode, and/or transmit the query data. In the example of system 100 of FIG. 1, query data may be received by local computing system 150 from genomic sample data source 130. In some embodiments, query data may be transferred in accordance with network communication, physical media, and/or any of the other data communication techniques discussed herein.

In some embodiments, the query data may be received in association with metadata, including metadata identifying an organism represented by the genomic reference data and/or including any of the metadata discussed above with respect to genomic sample data source 130 in FIG. 1. In some embodiments, when metadata associated with the query data identifies or purports to identify a known, suspected, and/or estimated identity of the query data, the techniques discussed herein may nonetheless be used to validate and/or supplement that identification.

At block 236, in some embodiments, for each of the plurality of query nucleic acid sequences, the query nucleic acid sequence may be divided into a plurality of query sub-strings. At block 238, in some embodiments, the query sub-strings are of predetermined length k, where k is the number of bases in a sub-string. At block 240, in some embodiments, the query nucleic acid sequence is divided into (L−k+1) sub-strings, where L is the number of bases in the query nucleic acid sequence.

In some embodiments, the division process (e.g., "k-merization" process) of blocks 236-240 may share some or all properties in common with the division process discussed above at blocks 206 to 210, except that the process may here be applied to query nucleic acid sequences rather than to reference nucleic acid sequences and that the process here may in some embodiments be carried out by a different computer system than for the reference nucleic acid sequences. In the example of system 100 of FIG. 1, the division process may be executed by local computing system 150, acting on query genomic nucleic acid sequences received from genomic sample data source 130.

In some embodiments, the query sub-strings created from the query nucleic acid sequence may be created to have the same length k as the reference sub-strings, such that the system may search for identical sub-strings of length k that can be found both in a reference nucleic acid sequence and in the query nucleic acid sequence. In some embodiments, the total number of sub-strings created from any one query nucleic acid sub-string may be the same or may be different from the total number of sub-strings created from any one reference nucleic acid sequence; for example, if a reference nucleic acid sequence is WGS data, then its length L may be significantly longer than the length L of a query nucleic acid sequence found in a read-set, and the number of query sub-strings may therefore be lower than the number of reference sub-strings.

At block 242, in some embodiments, for each of the plurality of query nucleic acid sequences, data representing one or more of the plurality of query sub-strings may be stored. At block 244, in some embodiments, data representing only unique query sub-strings may be stored. At block 246, in some embodiments, storing data representing one or more of the plurality of query sub-strings comprises generating and storing data corresponding to a reverse compliment of one or more of the query sub-strings.

In some embodiments, the storage processes of blocks 242-246 may share some or all properties in common with the storage processes discussed above at blocks 212-216, except that the process may here be applied to query sub-strings rather than to reference sub-strings, and that the processes here may in some embodiments be carried out by a different computer system than for the reference sub-strings. As with blocks 212-216, an indication of how many times a unique sub-string is encountered in the data may be stored in association with the data reflecting the unique sub-string itself. In the example of system 100 of FIG. 1, the storage processes may be executed by local computing system 150, storing query sub-strings generated based on the query genomic nucleic acid sequences received from genomic sample data source 130.

It should be noted that, since block 242 is performed "for each of the plurality of query nucleic acid sequences," the process in block 246 that stores only unique sub-strings may be applied on a per-nucleic-acid-sequence basis, rather than on a basis of an entire body of genomic sample data. In some embodiments, the sub-strings may be de-duplicated in accordance with the process of block 246 on a per-nucleic-acid-sequence basis, on a per-read basis, on a per-read-set basis, and/or on a per-sample basis.

At block 248, in some embodiments, blocks 250-254 may represent steps performed for each of the plurality of probabilistic data structures received. For each one of the plurality of probabilistic data structures, blocks 250-254 may be applied iteratively or concurrently/in parallel for each individual probabilistic data structure. (As such, each of blocks 250-254 may refer to a specific probabilistic data structure and its respective set of reference sub-strings.) As explained below, applying these processes for of the plurality of probabilistic data structures received may enable query genomic data to be compared to tens of thousands or hundreds of thousands or more probabilistic data structures in order to identify the closest matches for the unidentified query data and to thereby quickly and effectively determine one or more most probable identities for organisms/species/strains associated with the unidentified query nucleic acid sequences from among the tens of thousands or hundreds of thousands or more identities associated with the reference nucleic acid sequences.

At block 250, in some embodiments, the probabilistic data structure may be queried by data comparing each of the one or more of the plurality of query sub-strings of the query nucleic acid sequence. In general, in some embodiments, querying the probabilistic data set comprises comparing one or more pieces of information against the probabilistic data set in order to determine whether the piece of information is probably included in the probabilistic data structure or alternately whether it is definitely not included in the probabilistic data structure. In some embodiments, one or more indications may be generated and stored to indicate whether the probabilistic data structure indicates likely inclusion or certain exclusion for any given query.

In the example of system 100 of FIG. 1, the querying may be performed by local computing system 150 and may include using each of the one or more of the plurality of query sub-strings as input data for comparison with the probabilistic data structure. The system and probabilistic data structure may be configured, as discussed below, to generate in response to the querying a determination as to whether the data used for the querying is likely included in the set represented by the probabilistic data structure.

At block 252, in some embodiments, in response to the querying by each of the one or more query sub-strings, result data may be generated and stored indicating whether the set of reference sub-strings includes data corresponding to each of the respective query sub-strings. In the example of system 100 of FIG. 10, the generated and/or calculated data may be stored on storage 111 of local computing system 150 and/or may be transmitted to any other computer system or computer storage medium.

In some embodiments, the result data generated may indicate the result of a determination as to whether data corresponding to each of the query sub-strings is likely included in the set of reference sub-strings represented by the probabilistic data structure. This query/comparison process may be used to determine whether each of a plurality of query sub-strings are likely found in the set of reference sub-strings that was used to create the probabilistic data structure. In this way, querying the probabilistic data structure built based on a set of reference k-mers may be used to determine what query k-mers are likely also present in the set of reference k-mers. Thus, the data generated may constitute an indication as to whether an unidentified query sub-string is likely also present in the set of known reference sub-strings, thereby indicating that the same k-mer likely appears in the reference nucleic acid sequence and in the query nucleic acid sequence.

At block 254, in some embodiments, the proportion of query sub-strings that correspond to one or more of the reference sub-strings represented by the probabilistic data structure is calculated, and data reflecting this proportion may be stored and/or transmitted. In the example of system 100 of FIG. 10, the generated and/or calculated data may be stored on storage 111 of local computing system 150 and/or may be transmitted to any other computer system or computer storage medium. In some embodiments, other coverage metrics related to or similar to the proportion of reference sub-strings that correspond to any one of the respective query sub-strings may similarly be calculated, stored, and/or transmitted.

In some embodiments, a system may compare each one of a plurality of unidentified query sub-strings associated with the query nucleic acid sequence against the probabilistic data structure that was built based on the set of sub-strings extracted from an identified reference nucleic acid sequence. The system may generate and store an indication of whether the probabilistic data structure indicates likely inclusion or definite exclusion for each one of the query sub-strings that are so compared, and the system may further calculate coverage metrics for the entire plurality of query sub-strings associated with one query nucleic acid sequence and/or associated with one body of unidentified genomic sample data. For example, the system may calculate a percentage of the query sub-strings for which the probabilistic data structure indicated likely inclusion, and/or the system may calculate a percentage of the query sub-strings for which the probabilistic data structure indicated definite exclusion. After comparing all reference sub-strings associated with one reference nucleic acid sequence and/or one body of genomic reference data against a probabilistic data structure representing a reference nucleic acid sequence, the system may thus generate an output indicating the overall proportion or percentage of the query sub-strings that are indicated as likely also appearing as sub-strings in the reference nucleic acid sequence that is represented by the probabilistic data structure.

In some embodiments, if a large number (e.g., a high percentage, such as more than 90%, more than 95%, or more than 99%) of query k-mers are found to be likely to be present in the set of reference k-mers, then the query nucleic acid sequence and/or the genomic sample data may be determined to be genetically associated with the reference genome, such as being of the same species or the same strain, or including genetic material attributable to an organism of the same species or the same strain.

In some embodiments, calculating coverage or a degree of matching of a probabilistic data structure to query data may include calculating and/or outputting a total number of matching sub-strings, in place of or in addition to outputting a proportion or percentage.

In some embodiments, calculating coverage metrics such as a number of matching sub-strings and/or a proportion of matching sub-strings may include accounting for sub-strings that appear multiple times in either the original reference nucleic acid sequence or in the original query nucleic acid sequence or query data (e.g., read-set). For example, if a record is stored indicating the number of times that a specific sub-string appeared in an original nucleic acid sequence, then the total number of matching sub-strings indicated by the probabilistic data structure comparison may be multiplied or otherwise weighted in accordance with the stored number of occurrences of the sub-string in the original nucleic acid sequence. In this manner, file size and processing speed may be optimized by not unnecessarily storing duplicate sub-strings, but result data accounting for the strength of coverage and/or matching may be correctly calculated in light of sub-strings that appear multiple times in a reference nucleic acid sequence and/or multiple times in read-set data or other genomic sample data or query data.

In some embodiments, the process discussed above with respect to blocks 248-254 may be iteratively and/or concurrently applied to each one of the probabilistic data structures in the plurality of probabilistic data structures, such that all query sub-strings in a body of genomic sample data may be compared against each and every one of the probabilistic data structures accessible by a system. In some embodiments, this may mean that the query sub-strings are compared against thousands, tens of thousands, or hundreds of thousands or more probabilistic data structures in order to search for the closest matches for the unidentified query data. In some embodiments, query sub-strings may be compared against all known or all accessible probabilistic data structures, while in some embodiments they may be compared only against a sub-set of accessible probabilistic data structures. For example, metadata associated with the probabilistic data structures may be used to pre-filter the probabilistic data structures before comparisons are made, such that only probabilistic data structures representing certain kinds of organisms, certain kinds of data, certain quality of data, or associated with certain parties or organizations may be included in the plurality of probabilistic data structures for comparison.

In some embodiments where a plurality of probabilistic data structures are each compared to a plurality of query sub-strings, the system may output an indication of the probabilistic data structures to which the plurality of query sub-strings have the largest number and/or the highest proportion of matching sub-strings and may rank the probabilistic data structures according to that proportion. By looking at the highest-ranked probabilistic data structures, the system or a user of the system may glean a prediction as to an identification/identity of one or more organisms associated with the query sub-strings, such as by assuming that the query sub-strings are attributable to a same organism, species, or strain as one or more of the probabilistic data structures to which the plurality of query sub-strings have the largest number and/or the highest proportion of matching sub-strings.

In some embodiments, rather than comparing individual query sub-strings to each of the probabilistic data structures, the query sub-strings themselves may be used to create an additional probabilistic data structure, which may itself be compared directly to the plurality of probabilistic data structures built from the genomic reference data. The result of such a comparison may be an index of similarity of the compared probabilistic data structures, such as a Jaccard index. This technique is explained, for example, in U.S. Provisional patent application Ser. No. 62/505,376, filed May 12, 2017, titled "Secure Communication of Sensitive Genomic Information Using Probabilistic Data Structures," which is hereby incorporated in its entirety.

While method 200 has been explained with exemplary reference to identification of an identity (e.g., organism, species, strain, etc.) of unidentified/unclassified genomic sample data, the method may be adapted to be used to identify other characteristics (aside from taxonomic identity) in unidentified/unclassified genomic sample data. For example, in some embodiments, probabilistic data structures may be created based on genomic reference data (e.g., nucleic acid sequences) that is known to be associated with certain traits, such as antibiotic resistance or characteristics of engineered (e.g., lab-generated) sequences. By comparing unidentified and/or unclassified genomic sample data to such probabilistic data structures, it may then be determined whether it is likely that the unidentified and/or unclassified genomic sample data contains any of the same sub-strings as the reference data, and it may be predicted whether the organisms associated with the unidentified and/or unclassified genomic sample data may be likely to express any of the same traits (e.g., antibiotic resistance).

Example 1—Pathogen Identification

The traditional approach to pathogen identification is costly and requires a suite of tests in order to ensure that the identification is accurate and the correct treatments are prescribed. If the identity of the microbe and its ABR profiles are inconclusive, this often leads to inappropriate treatments, which might seriously affect patient outcome. Overprescription of and the use of untargeted antibiotics have been linked to rising mutation rates, resulting in the emergence of additional resistance and even multiple resistance of bacteria to various antibiotics. The use of recent advances in bioinformatics—leveraged with the readily available vast amount of genomic data—provides an opportunity to reduce the overall cost and time needed to identify and determine ABR profiles. A successful solution includes a technical approach that balances accuracy and speed in diagnosis with an intuitive and easy-to-use interface. By combining modern bioinformatics techniques, statistical modelling, data analytics, and machine learning, this approach enables healthcare providers to correctly identify pathogens and determine which antibiotics are best suited to treat the pathogen. This solution incorporates the above techniques into a unified process.

A WGS data and bioinformatics analysis pipeline may be built. The pipeline may include a process that accepts sequence data as input and returns the pathogen causing the infection, its antibiotic resistance genes, a list of antibiotics used to eliminate the organism, and a sequence-based determination of whether the organism is possibly resistant or sensitive to each antibiotic.

Genomic sequence data formatted as probabilistic data structures, such as Bloom filters, may be used to filter out possible organisms. This process may result in a most-likely organism identity based on the matches found in the data structure. Once this identification is completed, and if the organism is bacterial, the sequences may then be passed through a second set of Bloom filters to determine genes indicative of antibacterial resistance. Based on these findings, a clinician may be able to identify antibiotics that are most likely to be effective based on the presence or absence of ABR genes.

Bloom filters may be built off the organism reference data from National Center for Biotechnology Information (NCBI). Each Bloom filter may represent a different genus or species. As the sequence is broken into k-mers and checked across Bloom filters, only k-mers that likely match the species represented by the Bloom filter may be signaled as a match. The organism that has the highest hit rate with the read set may be statistically more likely to be the correct organism.

Once the likely organism or organisms has been identified, the same process of finding genomic features indicating ABR may begin. In this portion of the pipeline, each Bloom filter may represent sequences that have been identified as ABR on a per-antibiotic basis. Such Bloom filters may be created based on genomic data from the Comprehensive Antibiotic Resistance Database and Antibiotic Resistance Database. A positive result from this stage may render one of two possible outcomes: the organism is antibiotic resistant or the gene is present for ABR but its expression is unknown. If an organism lacks resistance to a specific antibiotic, that is an antibiotic that would be effective against it. If a resistance mechanism is present, traditional testing methods may be required to accurately prescribe an antibiotic. This approach, leveraging whole genome sequencing and statistical analysis, may allow identification quickly and with a high degree of confidence.

The identification pipeline may leverage a Bloom filter library. A Bloom filter library must be able to save and reload previously generated filters, it must be performant in insertion and lookup, and it must allow for using different hashing algorithms as needed. It may also be beneficial for the library to be parallelizable for construction to reduce time in creating the Bloom filter index. Reference data from NCBI may be used to build up the reference Bloom filters for use in identification.

Relevant genomic features may be identified for inclusion in Bloom filters. For example, features identified through the National Antimicrobial Resistance Monitoring System (NARMS) may be used. These features may be annotated with mechanism of action to determine which bacterial types could be able to obtain this resistance and which countermeasures would be ineffective.

Parameters or characteristics of the system or technique (e.g., k-mer length k) may be defined and/or refined in accordance with the use of simulated sequencing data and may be further refined using publicly available sequences. Simulated sequencing data may be used to create "spiked" samples, such that the accuracy and reliability of the system/technique to detect known resistance genes may be evaluated and improved. Blood samples used for the spike may be treated with broad spectrum antibiotics and tested for infection prior to spiking with the known ABR strains to verify that the ABR presence is unique. Furthermore, spiking with multiple organisms (metagenomic) may be used to simulate co-infections.

By simulating such situations, the effect of mutations or other modifications to the known genes on the effectiveness and accuracy of the system/technique may be evaluated. Simulated data based on the sample spikes may be modified with blinded mutations that affect known features from another bacterium. This approach may define a threshold where the analysis can and cannot detect resistance, as well as demonstrate how capably it can deal with novel sequences.

Third-generation sequencing technologies may achieve data collection at quick enough rates to improve the current techniques. Once ABR features have been identified following analysis of WGS data by the Bloom filters, the presence of these same genes may be verified using traditional Polymerase Chain Reaction (PCR). Unique signatures representing presence of these features may be created. This validation may provide a direct measurement of the accuracy and effectiveness of the techniques described herein. Ultimately, the pipeline may be able to ascertain the identity and resistance profile of sampled genetic material without developing new targeted PCR tests for each new ABR variant. This may allow for feature-based diagnostics in near-real-time, in turn allowing clinicians to select the most effective treatment protocols.

Although the description herein uses terms first, second, etc. to describe various elements, these elements should not be limited by the terms. These terms are only used to distinguish one element from another.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

What is claimed is:

1. A system for identifying genomic information in a computing environment remote from a database of genomic reference data, the system comprising:
   one or more hardware processors;
   a memory storing one or more programs, the one or more programs configured to be executed by the one or more hardware processors and including instructions to:
      receive encoded data representing genomic reference data of a plurality of organisms, wherein the encoded data comprises:
         a plurality of probabilistic data structures each corresponding respectively to an organism of the plurality of organisms, wherein each of the plurality of probabilistic data structures represents a respective plurality of elements as members of a set, wherein each of the plurality of elements corresponds to a nucleic acid sub-string of the genomic reference data of the respective organism; and
         metadata indicating an association of each of the plurality of probabilistic data structures with a respective one of the plurality of organisms;
      receive data representing a nucleic acid sequence;
      divide the data representing the nucleic acid sequence into a plurality of portions, wherein each of the plurality of portions represents a sub-string of the nucleic acid sequence; and
      for each of the plurality of probabilistic data structures in the encoded genomic reference data:
         query the probabilistic data structure by each of the plurality of portions of the data representing the nucleic acid sequence;
         generate, in response to querying the probabilistic data structure, result data comprising one or more indications of whether each of the plurality of portions of the data representing the nucleic acid sequence is a member of the set of sub-strings of the genomic reference data of the respective organism;
         store the result data in a data structure comprising an indication of the respective organism associated with the metadata associated with the probabilistic data structure; and
         calculate one or more coverage metrics, wherein calculating the one or more coverage metrics comprises calculating a percentage of the plurality of portions of the data representing the nucleic acid sequence that are determined to be members of the set of sub-strings of the genomic reference data of the respective organism.

2. The system of claim 1, wherein the one or more programs include instructions to, generate an output indicating the one or more organisms associated with the probabilistic data structures for which the calculated percentages are the highest among the probabilistic data structures in the encoded data.

3. The system of claim 1, wherein generating result data comprises one of generating data indicating that an element is definitely not a member of the set and generating data indicating that an element is probably a member of the set.

4. The system of claim 1, wherein each of the probabilistic data structures has a predefined false-positive probability.

5. The system of claim 4, wherein the predefined false-positive probability is set at least in part in accordance with available processing resources of the one or more hardware processors or of associated storage.

6. The system of claim 4, wherein the predefined false-positive probability is set at least in part in accordance with available storage resources associated with the one or more hardware processors.

7. The system of claim 4, wherein the predefined false-positive probability is set at least in part in accordance with requirements for accuracy of comparisons to be made against the probabilistic data structure.

8. The system of claim 1, wherein each of the plurality of probabilistic data structures is configured such that redundant reference sub-strings are represented as members of the respective set only once.

9. The system of claim 8, calculating the one or more coverage metrics comprises accounting for a number of times that one or more of the redundant sub-strings appeared in the genomic reference data.

10. The system of claim 1, wherein the one or more programs further include instructions to, for each of the plurality of probabilistic data structures in the encoded genomic reference data, if the percentage exceeds a predefined threshold percentage, determine that the nucleic acid sequence is genetically associated with the reference genome.

11. The system of claim 10, wherein determining that the nucleic acid sequence is genetically associated with the reference genome comprises determining that the nucleic acid sequence and the reference genome represent one or both of: a same species, and a same strain.

12. The system of claim 1, wherein the plurality of probabilistic data structures comprises, for each organism of the plurality of organisms, a suite of probabilistic data structures representing sub-strings of varying lengths.

13. The system of claim 12, wherein the one or more programs include instructions to, determine, based on querying multiple probabilistic data structures in one or more of the suites of probabilistic data structures, a consensus across the probabilistic data structures for multiple different sub-string lengths.

14. A method for identifying genomic information in a computing environment remote from a database of genomic reference data, the method comprising:
at a system comprising one or more processors and a memory:
receiving encoded data representing genomic reference data of a plurality of organisms, wherein the encoded data comprises:
a plurality of probabilistic data structures each corresponding respectively to an organism of the plurality of organisms, wherein each of the plurality of probabilistic data structures represents a respective plurality of elements as members of a set, wherein each of the plurality of elements corresponds to a nucleic acid sub-string of the genomic reference data of the respective organism; and
metadata indicating an association of each of the plurality of probabilistic data structures with a respective one of the plurality of organisms;
receiving data representing a nucleic acid sequence;
dividing the data representing the nucleic acid sequence into a plurality of portions, wherein each of the plurality of portions represents a sub-string of the nucleic acid sequence; and
for each of the plurality of probabilistic data structures in the encoded genomic reference data:
querying the probabilistic data structure by each of the plurality of portions of the data representing the nucleic acid sequence;
generating, in response to querying the probabilistic data structure, result data comprising one or more indications of whether each of the plurality of portions of the data representing the nucleic acid sequence is a member of the set of sub-strings of the genomic reference data of the respective organism;
storing the result data in a data structure comprising an indication of the organism associated with the metadata associated with the probabilistic data structure; and
calculating one or more coverage metrics, wherein calculating the one or more coverage metrics comprises calculating a percentage of the plurality of portions of the data representing the nucleic acid sequence that are determined to be members of the set of sub-strings of the genomic reference data of the respective organism.

15. A non-transitory computer-readable storage medium storing one or more programs for identifying genomic information in a computing environment remote from a database of genomic reference data, the one or more programs configured to be executed by one or more processors and including instructions to:
receive encoded data representing genomic reference data of a plurality of organisms, wherein the encoded data comprises:
a plurality of probabilistic data structures each corresponding respectively to an organism of the plurality of organisms, wherein each of the plurality of probabilistic data structures represents a respective plurality of elements as members of a set, wherein each of the plurality of elements corresponds to a nucleic acid sub-string of the genomic reference data of the respective organism; and
metadata indicating an association of each of the plurality of probabilistic data structures with a respective one of the plurality of organisms;
receive data representing a nucleic acid sequence;
divide the data representing the nucleic acid sequence into a plurality of portions, wherein each of the plurality of portions represents a sub-string of the nucleic acid sequence; and
for each of the plurality of probabilistic data structures in the encoded genomic reference data:

query the probabilistic data structure by each of the plurality of portions of the data representing the nucleic acid sequence;

generate, in response to querying the probabilistic data structure, result data comprising one or more indications of whether each of the plurality of portions of the data representing the nucleic acid sequence is a member of the set of sub-strings of the genomic reference data of the respective organism;

store the result data in a data structure comprising an indication of the organism associated with the metadata associated with the probabilistic data structure; and calculate one or more coverage metrics, wherein calculating the one or more coverage metrics comprises calculating a percentage of the plurality of portions of the data representing the nucleic acid sequence that are determined to be members of the set of sub-strings of the genomic reference data of the respective organism.

* * * * *